(12) United States Patent
Yang et al.

(10) Patent No.: US 10,338,001 B2
(45) Date of Patent: Jul. 2, 2019

(54) POROUS DETECTION SYSTEM, APPARATUS AND METHOD

(71) Applicant: INDUSTRIAL TECHNOLOGY RESEARCH INSTITUTE, Hsinchu (TW)

(72) Inventors: Shih-Wen Yang, Hsinchu (TW); Chi-Lin Wu, Hsinchu (TW); Wei-Ting Yen, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 68 days.

(21) Appl. No.: 15/390,837

(22) Filed: Dec. 27, 2016

(65) Prior Publication Data

US 2018/0174319 A1 Jun. 21, 2018

(30) Foreign Application Priority Data

Dec. 19, 2016 (TW) .............................. 105142051 A

(51) Int. Cl.
| | | |
|---|---|---|
| G06T 7/60 | (2017.01) | |
| G01N 15/14 | (2006.01) | |
| G01B 11/24 | (2006.01) | |
| G01N 21/88 | (2006.01) | |

(52) U.S. Cl.
CPC ................................ G01N 21/8851 (2013.01)

(58) Field of Classification Search
CPC ...... G01N 21/95; G01N 15/1456; G06T 7/60; G02F 1/13; G01B 11/00; G01B 11/002; G01B 11/306; G01B 11/2433; G01B 11/2441; G01J 3/48
See application file for complete search history.

(56) References Cited

U.S. PATENT DOCUMENTS

| | | | |
|---|---|---|---|
| 2002/0063808 A1* | 5/2002 | Chino | ...................... B41J 2/465 |
| | | | 349/2 |
| 2002/0191189 A1* | 12/2002 | Mestha | ...................... G01J 3/02 |
| | | | 356/402 |

FOREIGN PATENT DOCUMENTS

| | | |
|---|---|---|
| CN | 101846636 | 9/2010 |
| CN | 102829951 | 12/2012 |
| CN | 104380087 | 2/2015 |
| EP | 0181122 A2 * 5/1986 | ........... G01B 11/002 |

(Continued)

*Primary Examiner* — Patricia I Young
(74) *Attorney, Agent, or Firm* — Amin, Turocy & Watson LLP

(57) ABSTRACT

A system, apparatus and method for detecting a porous object are provided. The system includes a light emitting module, a detecting module and an analyzing module. The light emitting module emits light onto an object to be measured such that the light passes through a plurality of holes of the object. The detecting module has a porous plate having a plurality of non-circular holes and a plurality of photosensitive units respectively corresponding to the non-circular holes. Each of the non-circular holes corresponds to at most one of the holes at one time point. The light passes through the plurality of non-circular holes corresponding to the plurality of holes. The photosensitive units respectively sense luminous flux of the light passing through the plurality of non-circular holes to produce a luminous flux signal. The analyzing module analyzes a status of the plurality of holes corresponding to the plurality of non-circular holes.

24 Claims, 10 Drawing Sheets

(56) References Cited

FOREIGN PATENT DOCUMENTS

| | | |
|---|---|---|
| TW | 138117 | 7/1990 |
| TW | I226451 | 1/2005 |
| TW | I445310 | 7/2014 |

\* cited by examiner

POROUS DETECTION SYSTEM, APPARATUS AND METHOD

CROSS-REFERENCE TO RELATED APPLICATION

The present disclosure is based on, and claims priority from Taiwan Application Number 105142051, filed on Dec. 19, 2016, the disclosure of which is hereby incorporated by reference herein in its entirety.

BACKGROUND

1. Technical Field

The disclosure relates to systems, apparatuses and methods for detecting a porous object, and, more particularly, to a system, an apparatus and a method that employs non-circular holes for detecting a porous object.

2. Description of Related Art

Tiny nozzle holes are typically distributed on a spinneret used in a standard production process in the textile industry. Unimpeded nozzle holes are critical to the production of high-quality textile products. A conventional method for detecting blockage of the holes may include the use of an imaging device with CCDs (Charge-Coupled Devices) in order to capture and determine whether the nozzle holes are blocked one at a time point.

However, with the increasing demands for high-performance textiles and the increasing productivity of textiles in general, the densities of the nozzle holes are increasing and the distances between them become smaller and smaller. Therefore, using a CCD imaging device to determine the level of blockage in the nozzle holes is not only time consuming but also of poor detection accuracy.

Therefore, there is a need for a solution that addresses the aforementioned issues in the prior art.

SUMMARY

The present disclosure provides a system, an apparatus and a method for detecting a porous object.

In an embodiment, the system may include a light emitting module, a detecting module and an analyzing module. The light emitting module is used for emitting light onto an object to be measured such that the light passes through a plurality of holes of the object. The detecting module may include a porous plate having a plurality of non-circular holes and a plurality of photosensitive units respectively corresponding to the non-circular holes. Each of the non-circular holes of the porous plate corresponds to at most one of the holes of the object at one time point. The light passes through the plurality of non-circular holes of the porous plate corresponding to the holes of the object. The plurality of photosensitive units respectively sense luminous flux of the light passing through the plurality of non-circular holes of the porous plate to generate a luminous flux signal. The analyzing module is used for analyzing a status of the holes of the object corresponding to the non-circular holes of the porous plate based on the luminous flux signal generated by the photosensitive units.

In another embodiment, the apparatus may include a light emitting module and a detecting module. The light emitting module is used for emitting light onto an object such that the light passes through a plurality of holes of the object. The detecting module may include a porous plate having a plurality of non-circular holes and a plurality of photosensitive units respectively corresponding to the non-circular holes. Each of the non-circular holes of the porous plate corresponds to at most one of the holes of the object at one time point. The light passes through the plurality of non-circular holes of the porous plate corresponding to the plurality of holes of the object. The plurality of photosensitive units sense luminous flux of the light passing through the plurality of non-circular holes of the porous plate to generate a luminous flux signal.

In yet another embodiment, the method may include: providing a porous plate having a plurality of non-circular holes and a plurality of photosensitive units respectively corresponding to the plurality of non-circular holes, each of the non-circular holes of the porous plate corresponding to at most one of a plurality of holes of an object at one time point; emitting light onto the object such that the light passes through the plurality of holes of the object and respectively passes through the plurality of non-circular holes of the porous plate corresponding to the plurality of holes of the object; sensing, by the photosensitive units, luminous flux of the light passing through the plurality of non-circular holes of the porous plate to generate a luminous flux signal; and analyzing a status of the plurality of holes of the object corresponding to the plurality of non-circular holes of the porous plate based on the luminous flux signal generated by the plurality of photosensitive units.

BRIEF DESCRIPTION OF DRAWINGS

The invention can be more fully understood by reading the following detailed description of the preferred embodiments, with reference made to the accompanying drawings, wherein.

DETAILED DESCRIPTION

Figure 1A:
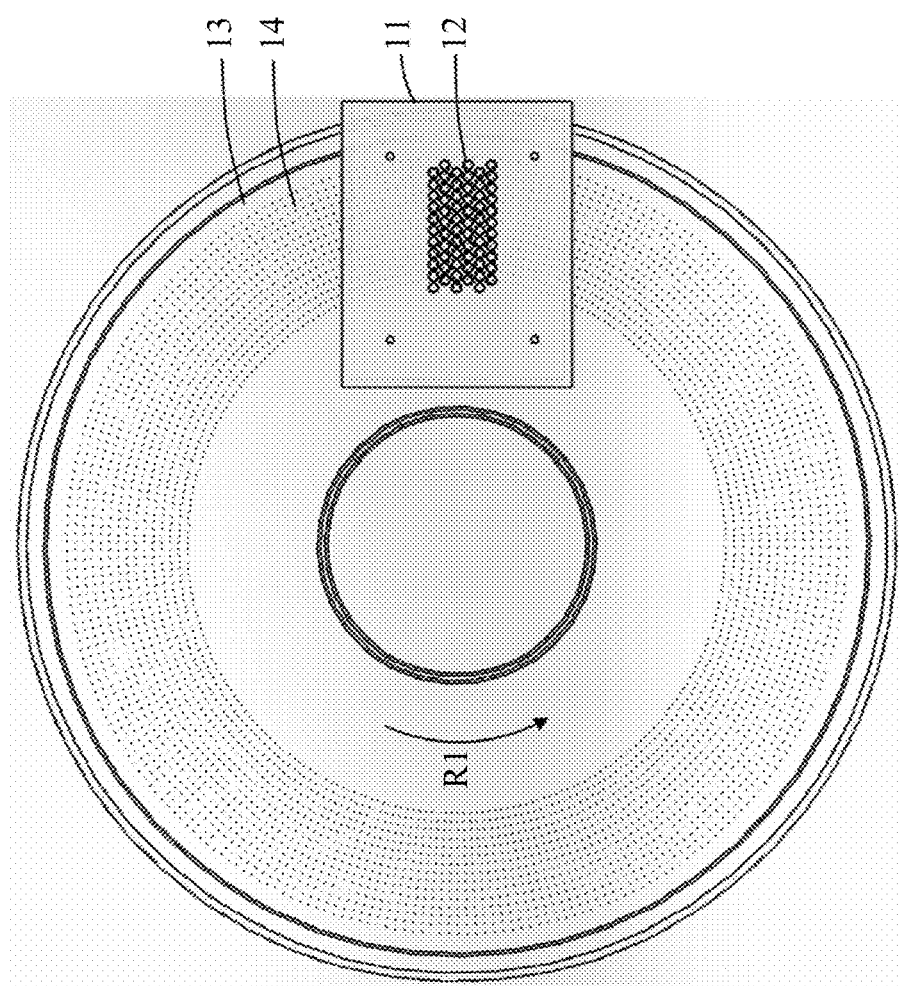
FIG. 1A is a top view depicting a porous plate having a plurality of circular holes for checking a plurality of nozzle holes of a spinneret in a system for detecting a porous object according to the conventional system.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1B:
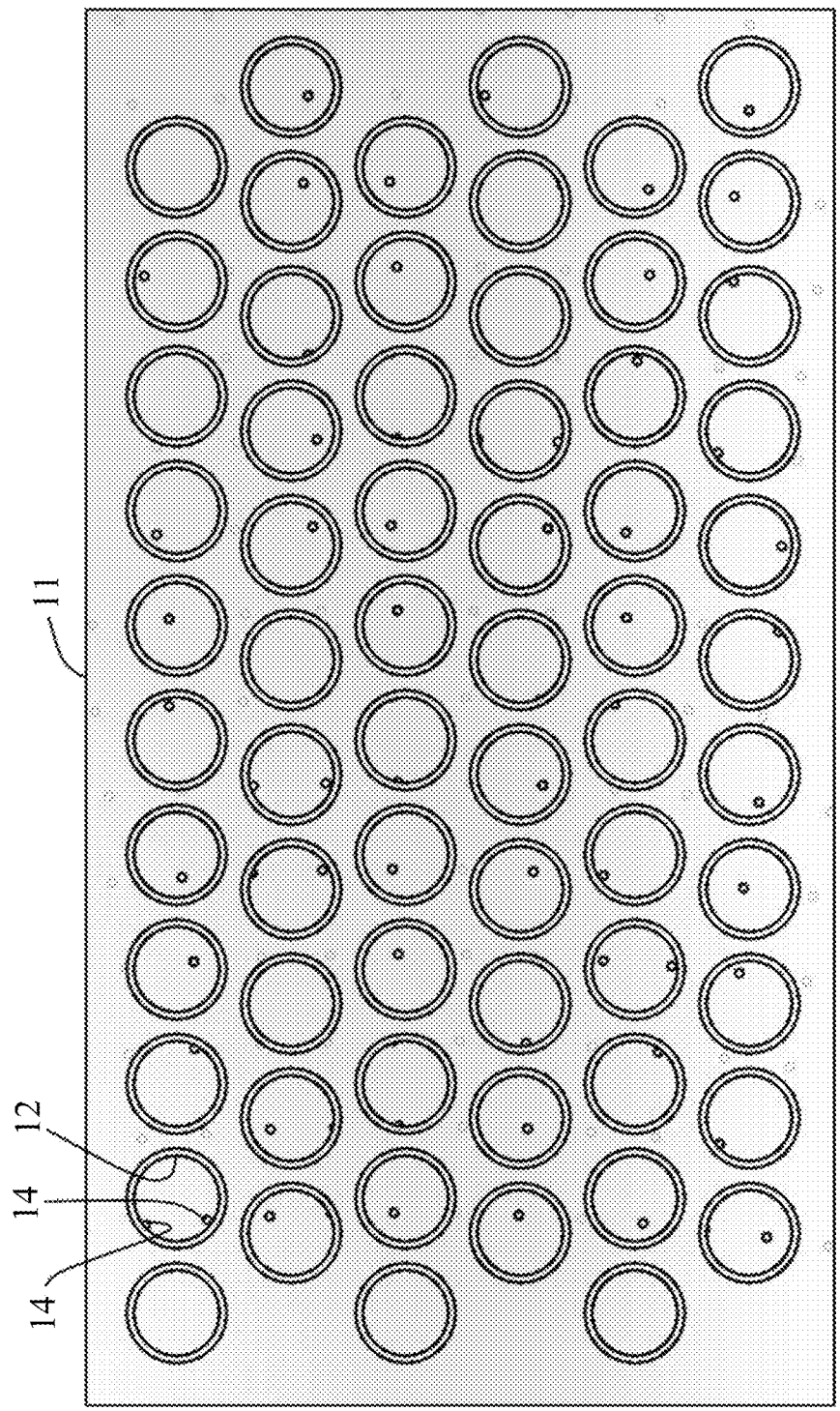
FIG. 1B is a partially enlarged view of the porous plate having the circular holes and the spinneret having the plurality of nozzle holes of FIG. 1A.
Figure 2:
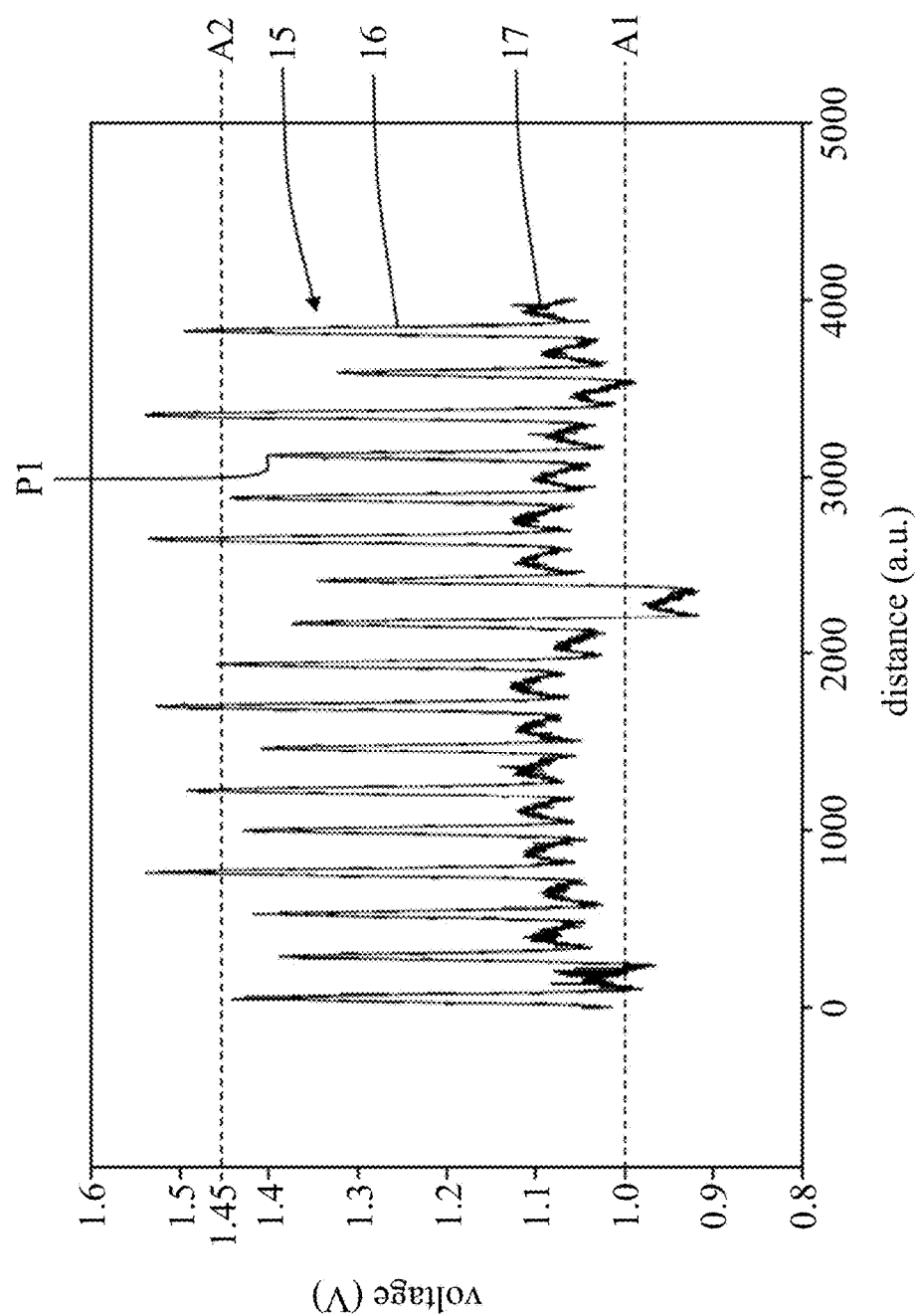
FIG. 2 is a graph depicting a waveform of a voltage signal obtained by detecting luminous flux passing through the nozzle holes of the spinneret by using the circular holes of the porous plate in a system for detecting a porous object according to the conventional system.

FIG. 1A is a top view depicting a porous plate 11 having a plurality of circular holes 12 for checking a plurality of nozzle holes 14 of a spinneret 13 in a system (not shown) for detecting a porous object according to the conventional system. FIG. 1B is a partially enlarged view of the porous plate 11 having the plurality of circular holes 12 and the spinneret 13 having the plurality of nozzle holes 14 of FIG. 1A. FIG. 2 is a graph depicting a waveform of a voltage signal 15 obtained by detecting luminous flux passing through the nozzle holes 14 of the spinneret 13 by using the circular holes 12 of the porous plate 11 in the system of FIG. 1A, and the unit of a distance indicated on the horizontal axis in the graph can be an arbitrary unit (a. u.).

As shown in FIGS. 1A and 1B, the system rotates the spinneret 13 in an angular direction R1 (e.g., in the anti-clockwise direction), and determines the level of blockage of the plurality of nozzle holes 14 of the spinneret 13 through the plurality of circular holes 12 of the porous plate 11.

However, a situation may occur in which a circular hole 12 of the porous plate 11 simultaneously corresponds to two of the plurality of nozzle holes 14 on the spinneret 13. In this case, light (not shown) will pass through the circular hole 12 of the porous plate 11 from the two nozzle holes 14 of the spinneret 13, which causes the voltage signal 15 obtained from the plurality of circular holes 12 of the porous plate 11 of the system to appear chaotic and noisy (indicated by reference number 17) (see FIG. 2).

Moreover, it can be seen from FIG. 2 that the average of voltage differences (e.g., voltage differences between line A2 and A1) between a plurality of pulses 16 in the voltage signal 15 is approximately 0.45 volts (V), that is, the average peak voltage (about 1.45V) of the plurality of pulses 16 minus the average trough voltage (about 1.0V) of the pulses 16 equals the average voltage difference (about 0.45V) of the plurality of pulses 16. This means that the luminous flux of light in FIGS. 1A to 1B passing through the plurality of circular holes 12 of the porous plate 11 from the plurality of the nozzle holes 14 of the spinneret 13 is less.

Figure 3:
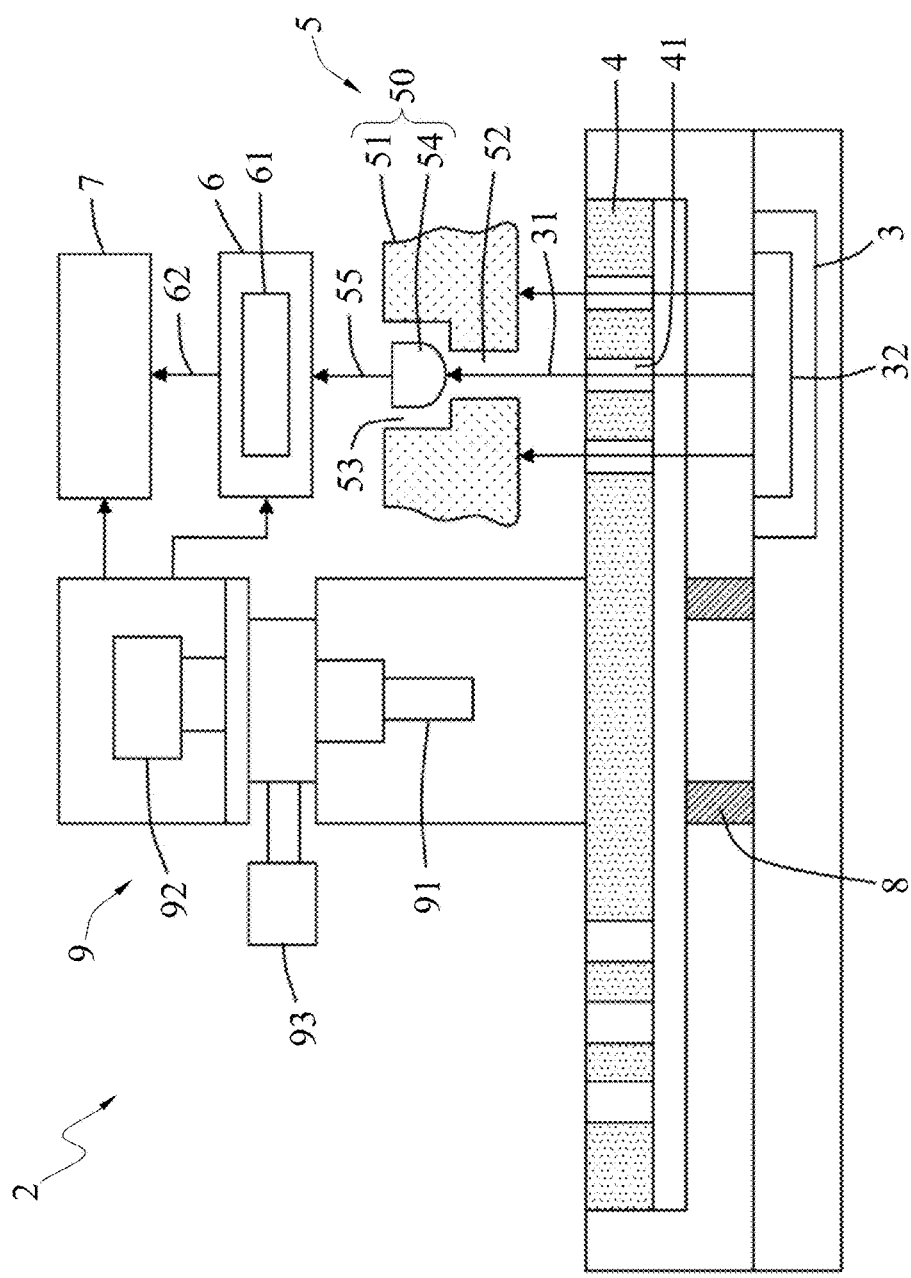
FIG. 3 is a block diagram depicting a system and an apparatus for detecting a porous object in accordance with the present disclosure, wherein only a portion of the apparatus is shown.
Figure 4:
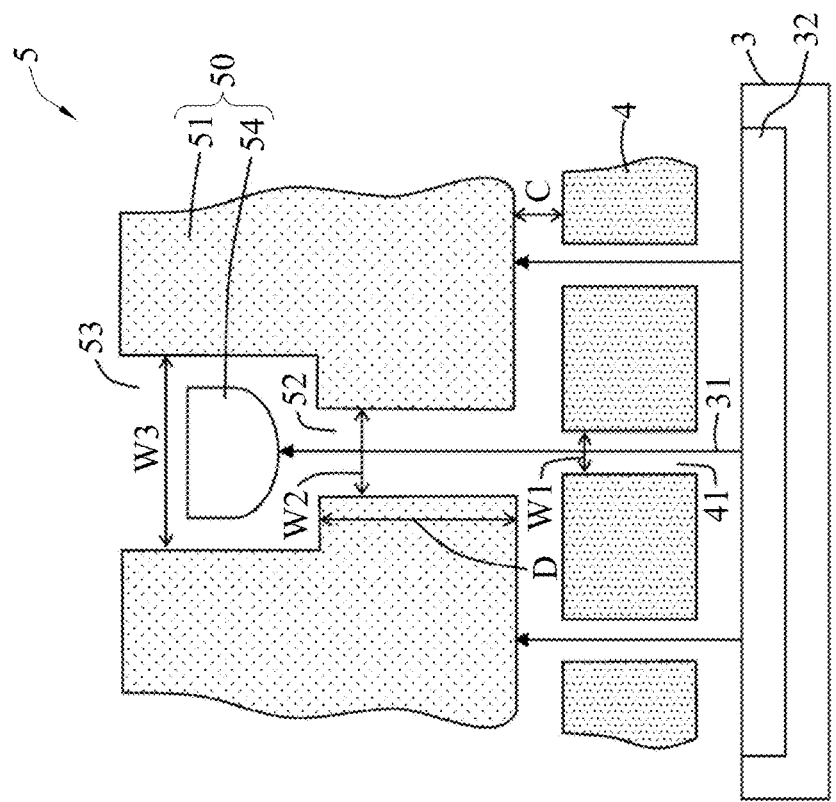
FIG. 4 is an enlarged view of the apparatus of FIG. 3 in accordance with the present disclosure.
Figure 5A:
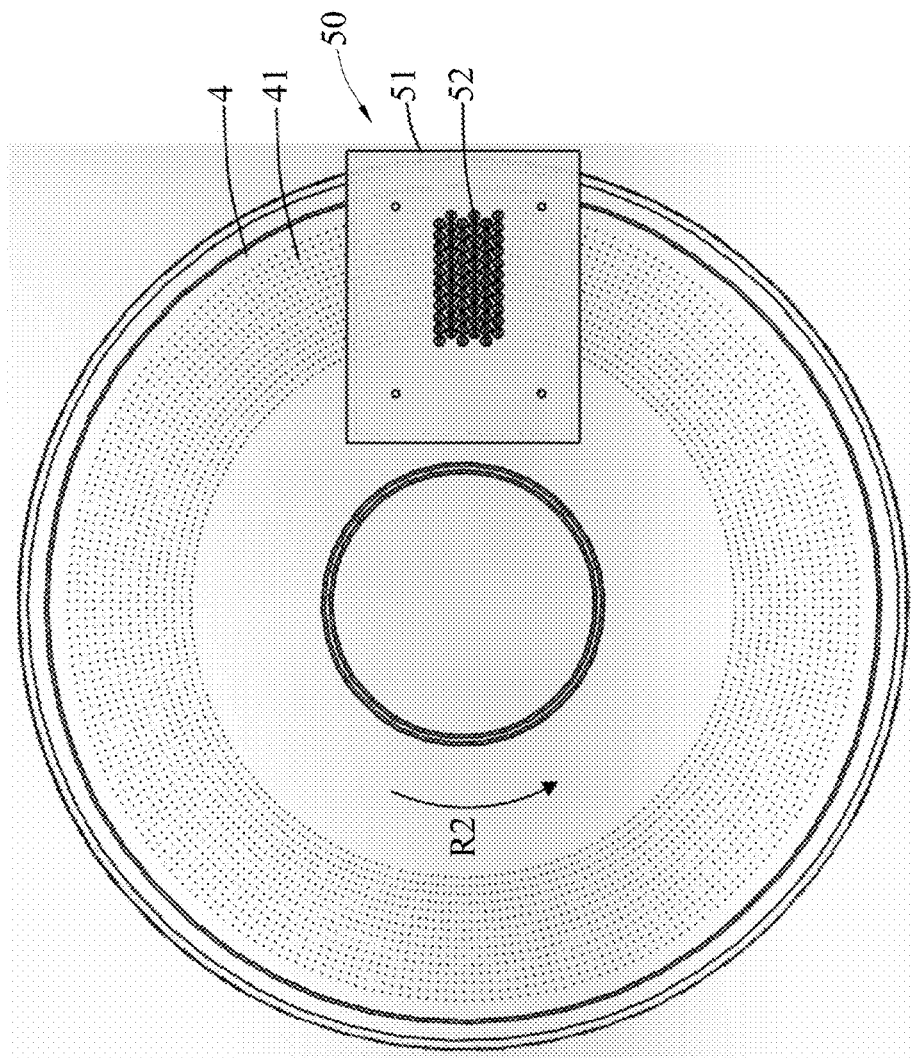
FIG. 5A is a top view depicting a porous plate having a plurality of non-circular holes for checking a plurality of holes of an object in the system and the apparatus in accordance with the present disclosure.
Figure 5B:
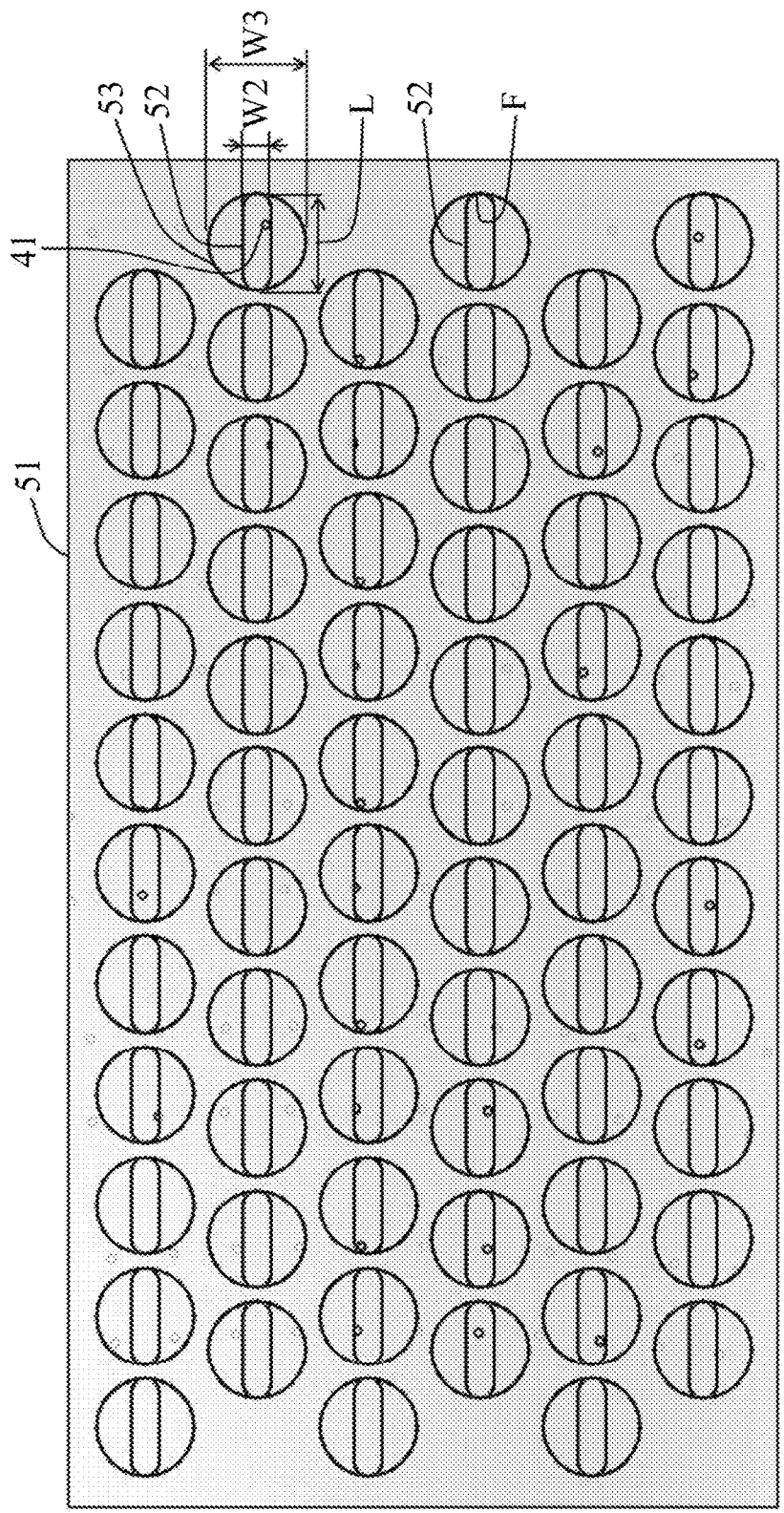
FIG. 5B is a partially enlarged view of the porous plate having the non-circular holes and the object having the holes of FIG. 5A.

FIG. 3 is a block diagram depicting a system 2 and an apparatus 5 for detecting a porous object in accordance with the present disclosure, wherein only a portion of the apparatus 5 is shown. FIG. 4 is an enlarged view of the apparatus 5 of FIG. 3 in accordance with the present disclosure. FIG. 5A is a top view depicting a porous plate 51 having a plurality of non-circular holes 52 for checking a plurality of holes 41 of an object 4 in the system 2 and the apparatus 5 in accordance with the present disclosure. FIG. 5B is a partially enlarged view of the porous plate 51 having the plurality of non-circular holes 52 and the object 4 having the plurality of holes 41 of FIG. 5A.

As shown in FIGS. 3 to 5B, the system 2 mainly includes the apparatus 5 and an analyzing module 6. The apparatus 5 further includes a light emitting module 3 and a detecting module 50. The light emitting module 3 and the detecting module 50 are disposed above and under the object 4, respectively. In addition to being a spinneret, the object 4 can also be a printed circuit board (PCB) with a plurality of holes or other objects.

The light emitting module 3 emits light 31 (a light source) that passes through the plurality of holes 41 of the object 4. The light emitting module 3 includes a divergence angle limiting unit 32 for reducing the divergence angle of the light 31, such that the light 31 is collimated before going into the plurality of holes 41 of the object 4.

The light emitting module 3 can be a backlight panel or made up of a plurality of light emitting diodes (LEDs) or halogen lamps. The light emitting module 3 provides light (light source) that is stable with wide-range, high brightness, high density or a smaller divergence angle. The holes 41 of the object 4 can be nozzle holes or tiny holes.

The detecting module 50 includes the porous plate 51 having the plurality of non-circular holes 52 and a plurality of photosensitive units 54. Each of the photosensitive units 54 corresponds to one of a plurality of non-circular holes 52. The photosensitive units 54 can be photosensitive elements or light detecting elements, such as photo diodes or photo detectors etc.

Each of the non-circular holes 52 of the porous plate 51 can only correspond to at most one of the plurality of holes 41 of the object 4 at one time point. The light 31 passes through the plurality of non-circular holes 52 on the porous plate 51 corresponding to the plurality of holes 41 of the object 4, and the plurality of photosensitive units 54 sense a luminous flux of the light passing through the plurality of non-circular holes 52 to generate luminous flux signals 55. The luminous flux of the light 31 can be the light intensity of the light 31, and the luminous flux signals 55 can be light intensity signals.

A width W2 (or an aperture size) of the plurality of non-circular holes 52 of the porous plate 51 can be greater than a width W1 (or an aperture size) of the plurality of holes 41 of the object 4. The plurality of non-circular holes 52 can be arranged in a regular or irregular order. The regular arrangement may be an array arrangement or a cross arrangement. One of the non-circular holes 52 can have the shape of a strip, for example, a long strip shape with two rounded edges F (see FIG. 5B). However, in other embodiments, the shape of a non-circular hole 52 may be a parallelogram (see FIG. 5C) or another different shape. Also, a length L of a non-circular hole 52 may be 1.5 to 4 times the width W2, so that each of the plurality of non-circular holes 52 can only correspond to at most one of the plurality of holes 41 of the object 4 at a particular time point.

The distance C between the porous plate 51 and the object 4 can be greater than 0 cm and less than 10 cm (i.e., 0<C<10). The depth D of the plurality of non-circular holes 52 can be more than double (e.g., three times) the width W2, so that the plurality of non-circular holes 52 have a high depth-width ratio. By doing so, stray light (e.g., stray light at the surroundings of the object 4 and the porous plate 51) other than the light 31 passing through the plurality of holes 41 can be prevented from entering between the porous plate 51 and the object 4 and pass through the plurality of non-circular holes 52, thereby improving the accuracy of luminous flux of the light 31 pass through the plurality of non-circular holes 52 sensed by the photosensitive units 54.

The analyzing module 6 is electrically connected to the plurality of photosensitive units 54 for analyzing a status of the plurality of holes 41 of the object 4 corresponding to the plurality of non-circular holes 52 of the porous plate 51 based on the luminous flux signals 55 generated by the plurality of photosensitive units 54. For example, the status may include whether the plurality of holes 41 are in good or bad condition, or the level of blockage, the degree of light transmission, the degree of damage or the degree of expansion/shrinkage, or surface roughness or material variability of the plurality of holes 41 etc.

The porous plate 51 may include a plurality of openings 53 respectively in communication with the non-circular holes 52. The size (e.g., width W3 or aperture size) of the openings 53 is greater than the size (e.g., width W2 or aperture size) of the non-circular holes 52, and the photosensitive units 54 are respectively disposed in the openings 53, each of which corresponds to one of the non-circular holes 52. However, in other embodiments, the porous plate 51 does not have the openings 53, and the photosensitive units 54 are respectively disposed in the plurality of non-circular holes 52.

The analyzing module 6 may include a signal conversion unit 61. The signal conversion unit 61 can convert the luminous flux signals 55 generated by the plurality of photosensitive units 54 into electrical signals (such as voltage signal 62 or current signals etc.), such that the analyzing module 6 may analyze the status of the plurality of holes 41 of the object 4 corresponding to the plurality of non-circular holes 52 of the porous plate 51 based on the electrical signals (such as voltage signal 62 or current signals). The analyzing module 6 may be analyzing equipment (e.g., a computer), analyzing software or the like. The signal conversion unit 61 may be a signal converter, a signal processor, a signal converting software, a signal processing software or the like.

As shown in FIG. 3, the system 2 may include an image capturing module 9 having a lens unit 91, an image photosensitive unit 92 and an indicating unit 93 (e.g., an indicating element). The lens unit 91 and the image photosensitive unit 92 may capture images of the plurality of holes 41 of the object 4. The indicating unit 93 may point out a problematic (e.g., blocked) hole 41, and a user or the analyzing module 6 can then determine the status (e.g., level of blockage) of the plurality of holes 41 based on the images of the plurality of holes 41 captured by the image photosensitive unit 92 or images pointed out by the indicating unit 93. The lens unit 91 can be a lens group or the like. The image photosensitive unit 92 can be an image sensor or the like. The indicating unit 93 can be an indicating element, an indicator or the like.

The system 2 may include a rotating module 8 under the object 4. The rotating module 8 rotates the object 4 in an angular direction R2, so that all of the holes 41 of the object 4 will successively pass under the plurality of non-circular holes 52 of the porous plate 51, and the photosensitive units 54 successively sense the luminous flux of the light 31 passing through the plurality of non-circular holes 52 in order to generate the luminous flux signals 55. This allows the analyzing module 6 to analyze a status of the plurality of holes 41 corresponding to the plurality of non-circular holes 52 based on the luminous flux signals 55 or the electrical signals (e.g., the voltage signal 62 or current signals). The rotating module 8 can be a rotating mechanism. The angular direction R2 can be the anticlockwise or clockwise direction.

The system 2 may include a display module 7 electrically connected with the analyzing module 6 and the image capturing module 9. The display module 7 is used for displaying the luminous flux signals 55 or the electrical signals (e.g., the voltage signal 62 or current signals) analyzed by the analyzing module 6, and the images of the plurality of holes 41 captured by the image capturing module 9. The display module 7 can be a display, a display panel, a display screen or etc.

Figure 5C:
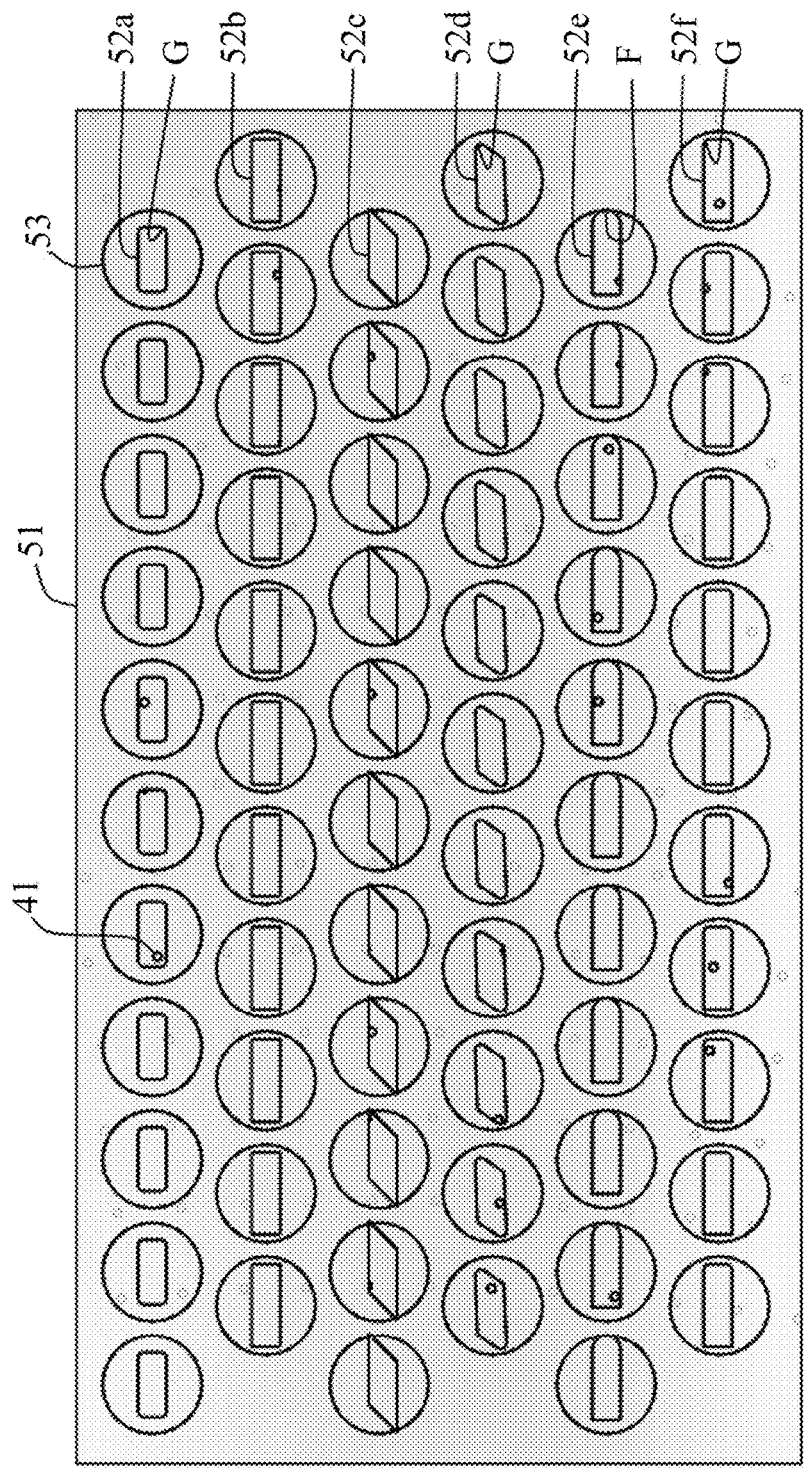
FIG. 5C is a schematic diagram depicting various aspects of the non-circular holes of FIG. 5B in accordance with the present disclosure.

FIG. 5C is a schematic diagram depicting various aspects of the plurality of non-circular holes 52 of FIG. 5B in accordance with the present disclosure, and the plurality of non-circular holes 52 of FIG. 5B can be replaced by any of the plurality of non-circular holes 52a to the plurality of non-circular holes 52f.

As shown in FIG. 5C, a non-circular hole 52a has a long strip shape with four chamfers G; a non-circular hole 52b has a long strip shape (i.e., a rectangular shape); a non-circular hole 52c has a parallelogram shape; a non-circular hole 52d has a parallelogram shape with two chamfers G; a non-circular hole 52e has a long strip shape with one round edge; and a non-circular hole 52f has a long strip shape with two chamfers G.

Figure 6:
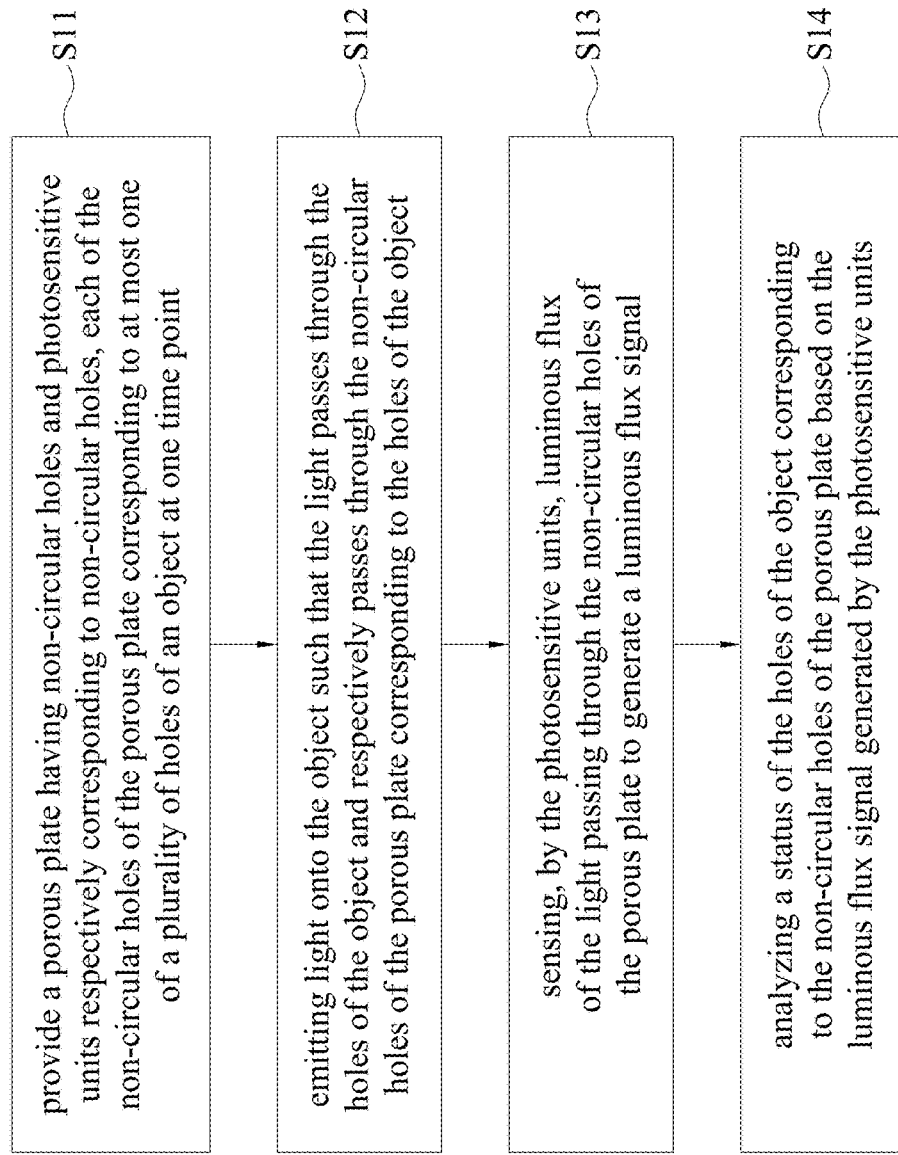
FIG. 6 is a flowchart illustrating a method for detecting a porous object in accordance with the present disclosure.

FIG. 6 is a flowchart illustrating a method for detecting a porous object in accordance with the present disclosure. Please refer to FIGS. 3 to 5C. The technical details of the method are similar to those described with respect to FIGS. 3 to 5C, so the steps of the method are briefly explained without repeating the same or similar technical aspects.

In step S11 of FIG. 6, a porous plate 51 having a plurality of non-circular holes 52 and a plurality of photosensitive units 54 corresponding to the plurality of non-circular holes 52 are provided, and each of the non-circular holes 52 of the porous plate 51 corresponds to at most one of a plurality of holes 41 of an object 4 at one time point.

The non-circular holes 52 of the porous plate 51 may have a long-strip shape, a parallelogram shape or etc. The non-circular holes 52 may include at least one rounded edge F or at least one chamfer G. The length L of the non-circular holes 52 may be 1.5 times to 20 times the width W2, or the depth D of the non-circular holes 52 may be more than double (e.g., three times) the width W2. The distance C between the porous plate 51 and the object 4 can be greater than 0 cm and less than 10 cm (i.e., 0<C<10). The porous plate 51 may include a plurality of openings 53 respectively in communication with the plurality of non-circular holes 52. The size (e.g., width W3 or aperture size) of the openings 53 is greater than the size (e.g., width W2 or aperture size) of the non-circular holes 52, and the photosensitive units 54 are respectively disposed in the openings 53, each corresponding to a non-circular hole 52.

In step S12 of FIG. 6, a light emitting module 3 emits light 31 that respectively passes through the plurality of holes 41 of the object 4, and the light 31 respectively pass through the plurality of non-circular holes 52 of the porous plate 51 corresponding to the plurality of holes 41 of the object 4.

In step S13 of FIG. 6, the photosensitive units 54 sense the luminous flux of the light 31 passing through the plurality of non-circular holes 52 to generate luminous flux signals 55.

In step S14 of FIG. 6, the analyzing module 6 analyzes a status of the plurality of holes 41 of the object 4 corresponding to the plurality of non-circular holes 52 of the porous plate 51 based on the luminous flux signals 55 generated by the plurality of photosensitive units 54.

A signal conversion unit 61 converts the luminous flux signals 55 generated by the photosensitive units 54 into electrical signals (e.g., voltage signal 62 or current signals), so that the analyzing module 6 can analyze a status of the plurality of holes 41 of the object 4 corresponding to the plurality of non-circular holes 52 of the porous plate 51 based on the electrical signals (e.g., voltage signal 62 or current signals).

Figure 7:
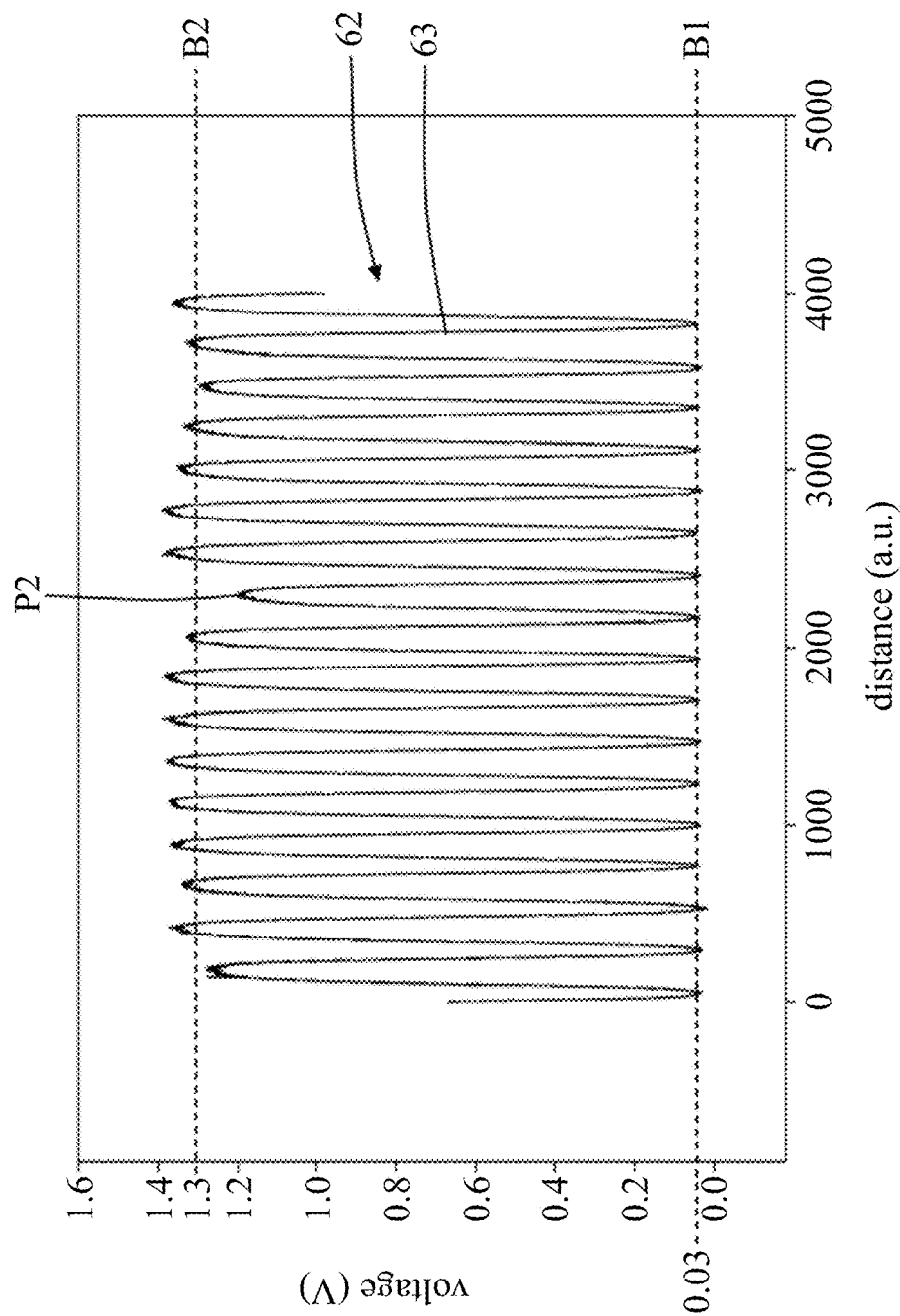
FIG. 7 is a graph of a waveform of a voltage signal obtained from the luminous flux passing through the object having the holes by using the porous plate having the non-circular holes in the system and the apparatus in accordance with the present disclosure.

FIG. 7 is a graph of a waveform of a voltage signal 62 obtained from the luminous flux passing through the object 4 having the plurality of holes 41 by using the porous plate 51 having the plurality of non-circular holes 52 with respect to FIGS. 3 to 6, wherein a distance shown on the horizontal axis of the graph can assume any arbitrary unit (a. u.), that is, there is no constraint on the unit used.

Measuring the same object 4, the average voltage difference (e.g., between line B2 and line B1) of a plurality of pulses 63 in the voltage signal 62 shown in FIG. 7 in accordance with the present disclosure is about 1.27V, that is, the average peak voltage (about 1.3V) of the plurality of pulses 63 minus the average trough voltage (about 0.03V) of the pulses 63 equals the average voltage difference (about 1.27V) of the plurality of pulses 63. On the contrary, the average of voltage differences (e.g., between line A2 and line A1) of a plurality of pulses 16 in the voltage signal 15 in FIG. 2 is approximately 0.45V, that is, the average peak voltage (about 1.45V) of the plurality of pulses 16 minus the average trough voltage (about 1.0V) of the plurality of pulses 16 equals the average voltage difference (about 0.45V) of the plurality of pulses 16. The voltage difference (about 1.27V) of the voltage signal 62 of FIG. 7 in accordance with the present disclosure is greater than the voltage difference (about 0.45V) of the voltage signal 15 of FIG. 2, which means that the luminous flux of light 31 passing through the plurality of non-circular holes 52 of the porous plate 51 is greater than the luminous flux of light passing through the plurality of circular holes 12 of the porous plate 11 in FIGS. 1A and 1B.

Similarly, under the circumstance of measuring the same object 4, the voltage signal 62 shown in FIG. 7 in accordance with the present disclosure is cleaner and less noisy, and the peaks P2 of only three pulses 63 do not exceed 1.3V, so the analyzing module 6 (such as analyzing software) can more accurately determine that the statues of only three holes 41 of the object 4 may have poorer condition (e.g., higher level of blockage). On the contrary, the voltage signal 15 shown in FIG. 2 is more chaotic and noisy 17, and the peaks of ten pulses 16 did not exceed 1.45V. As a result, the analyzing module 6 (analyzing software) may erroneously determine that these ten nozzle holes 14 in the spinneret 13 have poor status (e.g., higher level of blockage).

In conclusion, the system, the apparatus and the method for detecting a porous object in accordance with the present disclosure provide a porous plate with a plurality of non-circular holes, each of which corresponds to at most one of the plurality of holes in the object at one time point. Therefore, light passing from one of the holes of the object will pass through one of the non-circular holes of the porous plate. Therefore, the detecting module or analyzing module can obtain a larger luminous flux or voltage differences measured from the plurality of non-circular holes, and the luminous flux signal or the voltage signal is also cleaner and less noisy, thereby improving the detection accuracy of the status of the holes.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A system for detecting a porous object, comprising:
 a light emitting module configured for emitting light onto an object to be measured such that the light passes through a plurality of holes of the object;
 a detecting module including:
  a porous plate having a plurality of non-circular holes; and
  a plurality of photosensitive units respectively corresponding to the non-circular holes,
  wherein each of the non-circular holes of the porous plate corresponds to at most one of the holes of the object at one time point such that light passing from one of the holes of the object passes through one of the non-circular holes of the porous plate, the light passes through the non-circular holes of the porous plate corresponding to the holes of the object, and the photosensitive units sense luminous flux of the light passing through the non-circular holes of the porous plate to generate a luminous flux signal; and
 an analyzing module configured for analyzing a status of the holes of the object corresponding to the non-circular holes of the porous plate based on the luminous flux signal generated by the photosensitive units.

2. The system of claim 1, wherein the light emitting module includes a divergence angle limiting unit configured for narrowing a divergence angle of the light, such that the light is collimated before entering the holes of the object.

3. The system of claim 1, wherein one of the non-circular holes of the porous plate has a long-strip shape or a parallelogram shape.

4. The system of claim 1, wherein one of the non-circular holes of the porous plate has at least one rounded edge or at least one chamfer.

5. The system of claim 1, wherein one of the non-circular holes of the porous plate has a length 1.5 to 20 times its width.

6. The system of claim 1, wherein one of the non-circular holes of the porous plate has a depth more than double its width.

7. The system of claim 1, wherein the porous plate and the object are spaced apart at a distance greater than 0 cm and less than 10 cm.

8. The system of claim 1, wherein the porous plate further comprises a plurality of openings respectively in communication with the non-circular holes, the openings are greater than the non-circular holes in size, and the photosensitive units are respectively disposed in the openings.

9. The system of claim 1, wherein the analyzing module includes a signal conversion unit configured for converting the luminous flux signal generated by the photosensitive units into an electrical signal, and analyzes the status of the holes of the object corresponding to the non-circular holes of the porous plate based on the electrical signal.

10. An apparatus for detecting a porous object, comprising:
 a light emitting module configured for emitting light onto an object such that the light passes through a plurality of holes of the object; and
 a detecting module including:
  a porous plate having a plurality of non-circular holes; and
  a plurality of photosensitive units respectively corresponding to the non-circular holes,
  wherein each of the non-circular holes of the porous plate corresponds to at most one of the holes of the object at one time point such that light passing from one of the holes of the object passes through one of the non-circular holes of the porous plate, the light passes through the non-circular holes of the porous plate corresponding to the holes of the object, and the photosensitive units sense luminous flux of the light passing through the non-circular holes of the porous plate to generate a luminous flux signal.

11. The apparatus of claim 10, wherein one of the non-circular holes of the porous plate has a long-strip shape or a parallelogram shape.

12. The apparatus of claim 10, wherein one of the non-circular holes of the porous plate has at least one rounded edge or at least one chamfer.

13. The apparatus of claim 10, wherein one of the non-circular holes of the porous plate has a length 1.5 to 20 times its width.

14. The apparatus of claim 10, wherein one of the non-circular holes of the porous plate has a depth more than double its width.

15. The apparatus of claim 10, wherein the porous plate and the object are spaced apart at a distance greater than 0 cm and less than 10 cm.

16. The apparatus of claim 10, wherein the porous plate further comprises a plurality of openings respectively in communication with the non-circular holes, the openings are greater than the non-circular holes in size, and the photosensitive units are respectively disposed in the openings.

17. A method for detecting a porous object, comprising:
providing a porous plate having a plurality of non-circular holes and a plurality of photosensitive units respectively corresponding to the non-circular holes, each of the non-circular holes of the porous plate corresponding to at most one of a plurality of holes of an object at one time point such that light passing from one of the holes of the object passes through one of the non-circular holes of the porous plate;
emitting light onto the object such that the light passes through the holes of the object and respectively passes through the non-circular holes of the porous plate corresponding to the holes of the object;
sensing, by the photosensitive units, luminous flux of the light passing through the non-circular holes of the porous plate to generate a luminous flux signal; and
analyzing a status of the holes of the object corresponding to the non-circular holes of the porous plate based on the luminous flux signal generated by the photosensitive units.

18. The method of claim 17, wherein one of the non-circular holes of the porous plate has a long-strip shape or a parallelogram shape.

19. The method of claim 17, wherein one of the non-circular holes of the porous plate has at least one rounded edge or at least one chamfer.

20. The method of claim 17, wherein one of the non-circular holes of the porous plate has a length 1.5 to 20 times its width.

21. The method of claim 17, wherein one of the non-circular holes of the porous plate has a depth more than double its width.

22. The method of claim 17, wherein the porous plate and the object are spaced apart at a distance greater than 0 cm and less than 10 cm.

23. The method of claim 17, wherein the porous plate further includes a plurality of openings respectively in communication with the non-circular holes, the openings are greater than the non-circular holes in size, and the photosensitive units are respectively disposed in the openings.

24. The method of claim 17, further comprising converting the luminous flux signal generated by the photosensitive units into an electrical signal, and analyzing the status of the holes of the object corresponding to the non-circular holes of the porous plate based on the electrical signal.

\* \* \* \* \*